United States Patent [19]

Gsell et al.

[11] 4,144,330
[45] Mar. 13, 1979

[54] INSECTICIDAL S-TRIAZOLO-(1,5-A)-PYRIMIDIN-2-YL-5,7-DIMETHYL PHOSPHORIC ACID ESTERS AND AMIDES

[75] Inventors: Laurenz Gsell, Füllinsdorf; Willy Meyer, Riehen, both of Switzerland

[73] Assignee: Ciba-Geigy Corporation, Ardsley, N.Y.

[21] Appl. No.: 848,556

[22] Filed: Nov. 4, 1977

[30] Foreign Application Priority Data

Nov. 10, 1976 [CH] Switzerland ............ 14185/76
Sep. 29, 1977 [CH] Switzerland ............ 11908/77

[51] Int. Cl.² .............. C07D 403/04; A61K 31/505
[52] U.S. Cl. .................... 424/200; 544/243; 544/244; 544/263
[58] Field of Search ........... 260/256.5 R, 256.4 E; 424/200; 544/243, 244

[56] References Cited

U.S. PATENT DOCUMENTS

| | | | |
|---|---|---|---|
| 2,754,243 | 7/1956 | Gysin | 167/33 |
| 2,754,244 | 7/1956 | Gysin | 167/33 |
| 3,632,757 | 1/1972 | Scherer et al. | 424/200 |
| 3,966,730 | 6/1976 | Hofer | 260/251 P |
| 4,044,124 | 8/1977 | Boehner | 424/200 |

FOREIGN PATENT DOCUMENTS 1049960 11/1966 United Kingdom.

OTHER PUBLICATIONS

Chem. Abs.–Habu et al.; vol. 83:186297.

Primary Examiner—Nicholas S. Rizzo
Assistant Examiner—Lisa Jones
Attorney, Agent, or Firm—Frederick H. Rabin

[57] ABSTRACT

S-Triazolo-(1,5-a)-pyrimidin-2-yl-5,7-dimethyl-phosphoric acid derivatives of the formula

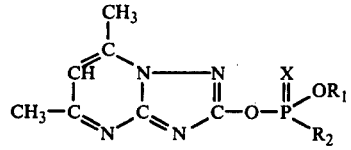

wherein
X represents oxygen or sulphur,
$R_1$ represents $C_1$–$C_6$-alkyl, and
$R_2$ represents $C_1$–$C_6$-alkyl, $C_1$–$C_6$-alkoxy, $C_1$–$C_6$-alkylthio, $C_1$–$C_6$-alkylamino or di-$C_1$–$C_6$-alkylamino, processes for producing them, and their use in combating pests.

12 Claims, No Drawings

INSECTICIDAL S-TRIAZOLO-(1,5-A)-PYRIMIDIN-2-YL-5,7-DIMETHYL PHOSPHORIC ACID ESTERS AND AMIDES

DETAILED DISCLOSURE

The present invention relates to S-triazolo-(1,5-a)-pyrimidin-2-yl-5,7-dimethyl-phosphoric acid derivatives, to processes for producing them, and to their use in combating pests.

The S-triazolo-(1,5-a)-pyrimidin-2-yl-5.7-dimethyl-phosphoric acid derivatives have the formula

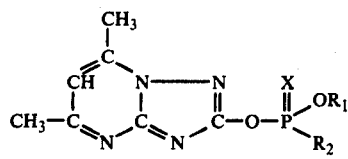

wherein
X represents oxygen or sulphur,
$R_1$ represents $C_1-C_6$-alkyl, and
$R_2$ represents $C_1-C_6$-alkyl, $C_1-C_6$-alkoxy, $C_1-C_6$-alkylthio, $C_1-C_6$-alkylamino or di-$C_1-C_6$-alkylamino.

The alkyl, alkoxy and alkylthio groups denoted by $R_1$ and $R_2$ can be straight-chain or branched-chain. Examples of such groups are, inter alia, methyl, methoxy, methylthio, ethyl, ethoxy, ethylthio, propyl, propoxy, propylthio, isopropyl, isopropoxy, isopropylthio, n-, i-, sec.- or tert.-butyl, n-pentyl, n-hexyl and isomers thereof.

Compounds of the formula I preferred by virtue of their action are those wherein x represents oxygen or sulphur; $R_1$ represents methyl, ethyl or n-butyl; and $R_2$ represents ethyl, methoxy, ethoxy, n-propylthio, isopropylamino or n-butoxy.

The compounds of the formula I can be produced by methods known per se, for example as follows:

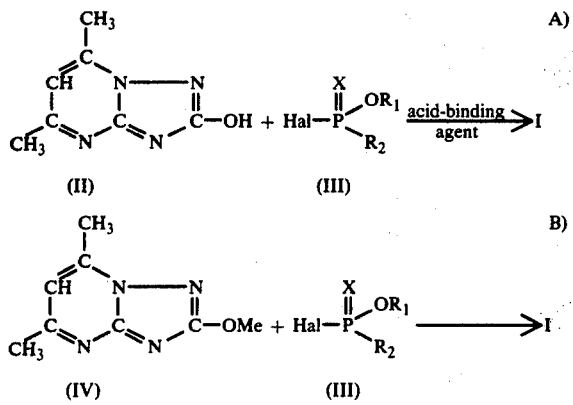

In the formulae III and IV, $R_1$, $R_2$ and X have the meanings given for the formula I, and "Hal" denotes halogen, preferably chlorine or bromine, and Me represents a metal, particularly an alkali metal, ammonium or trialkylammonium.

Suitable acid-binding agents are for example the following bases: tertiary amines such as triethylamine, dimethylaniline,, pyridine, and inorganic bases such as hydroxides and carbonates of alkali metals and alkaline-earth metals, preferably sodium carbonate and potassium carbonate.

The processes A and B are performed at a reaction temperature of 0°–120° C., preferably at 20°–80° C., under normal pressure and in solvents or diluents. Suitable solvents or diluents are, e.g., ethers and ethereal compounds, such as diethyl ether, dipropyl ether, dioxane, dimethoxyethane and tetrahydrofuran; amides such as N,N-dialkylated carboxylic acid amides; aliphatic, aromatic as well as halogenated hydrocarbons, particularly benzene, toluene, xylenes, chloroform and chlorobenzene; nitriles such as acetonitrile; dimethylsulphoxide, ketones such as acetone and methyl ethyl ketone, and water.

The starting materials of the formula III are known. They can be produced by processes analogous to known processes.

The starting materials of the formulae II and IV are novel, but they can be produced by known processes (see Example 1, wherein the production of a starting material of the formula II is described).

The compounds of the formula I are suitable for combating various animal and plant pests. These compounds are especially suitable for combating insects, and phytopathogenic mites and ticks, e.g., of the orders: Lepidoptera, Coleoptera, Homoptera, Heteroptera, Diptera, Acarina, Thysanoptera, Orthoptera, Anoplura, Siphonoptera, Mallophaga, Thysanura, Isoptera, Psocoptera and Hymenoptera.

The compounds of the formula I are particularly suitable for combating insects that damage plants, especially insects that damage plants by eating, in crops of ornamental plants and useful plants, particularly in cotton crops, (e.g., against *Spodoptera littoralis* and *Heliothis virescens*) and in crops of vegetables (e.g., against *Leptinotarsa decemlineata* and *Myzus persicae*). Active substances of the formula I have a very good action also against flies, such as *Musca domestica*, and against mosquito larvae.

The acaricidal and insecticidal action can be substantially broadened and adapted to suit given circumstances by the addition of other insecticides and/or acaricides. Suitable additives are, e.g., organic phosphorus compounds; nitrophenols and derivatives thereof; formamidines; ureas; other pyrethrinlike compounds; and also carbamates and chlorinated hydrocarbons.

Compounds of the formula I are combined particularly advantageously also with substances which have a synergistic or intensifying effect on pyrethroids. Examples of such compounds are, inter alia, piperonylbutoxide, propynyl ethers, propynyl oximes, propynyl carbamates and propynyl phosphonates, 2-(3,4-methylenedioxyphenoxy)-3,6,9-trioxaundecane (Sesamex or Sesoxane), S,S,S-tributylphosphorotrithioates and 1,2-methylenedioxy-4-(2-(octylsulphonyl)-propyl)-benzene.

Compounds of the formula I can be used on their own or together with suitable carriers and/or additives. Suitable additives can be solid or liquid and they correspond to the substances common in formulation practice, such as natural or regenerated substances, solvents, dispersing agents, wetting agents, adhesives, thickeners, binders and/or fertilizers.

The compositions according to the invention are produced in a manner known per se by the intimate mixing and/or grinding of the active substances of the formula I with suitable carriers, optionally with the addition of dispersing agents or solvents which are inert to the active substances. The active substances can be obtained and used in the following forms:
solid preparations:

dusts, scattering agents, granules, (coated granules, impregnated granules and homogeneous granules);
liquid preparations:
(a) water-dispersible concentrates of active substance: wettable powders, pastes or emulsions;
(b) solutions.

The content of active substance in the compositions described is between 0.1 and 95%; it is to be mentioned in this respect that with application from an aeroplane, or by other suitable devices, concentrations of up to 99.5% or even the pure active substance can be used.

The active substances of the formula I can be formulated for example as follows (parts are by weight):

Dusts

The following substances are used to produce a) a 5% dust and b) a 2% dust:
(a) 5 parts of active substance,
95 parts of talcum;
(b) 2 parts of active substance,
1 part of highly dispersed silicic acid,
97 parts of talcum.

The active substance is mixed and ground with the carriers.

Granulate

The following ingredients are used to produce a 5% granulate:
5 parts of active substance,
0.25 part of epichlorohydrin,
0.25 part of cetyl polyglycol ether,
3.50 parts of polyethylene glycol,
91 parts of kaolin (particle size 0.3–0.8 mm).

The active substance is mixed with epichlorohydrin and dissolved with 6 parts of acetone; the polyethylene glycol and cetyl polyglycol ether are then added. The solution obtained is sprayed onto kaolin and the acetone is evaporated off in vacuo.

Wettable powder

The following constituents are used to produce (a) a 40%, (b) and (c) a 25%, and (d) a 10% wettable powder:
(a) 40 parts of active substance,
5 parts of sodium lignin sulphonate,
1 parts of sodium dibutyl-naphthalene sulphonate,
54 parts of silicic acid;
(b) 25 parts of active substance,
4.5 parts of calcium lignin sulphonate,
1.9 parts of Champagne chalk/hydroxyethyl cellulose mixture (1:1),
1.5 parts of sodium dibutyl-naphthalene sulphonate,
19.5 parts of silicic acid,
19.5 parts of Champagne chalk,
28.1 parts of kaolin;
(c) 25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr,
46 parts of kaolin,
(d) 10 parts of active substance,
3 parts of a mixture of the sodium salts of saturated fatty alcohol sulphates,
5 parts of naphthalenesulphonic acid/formaldehyde condensate,
82 parts of kaolin.

The active substance is intimately mixed in suitable mixers with the additives, and the mixture is then ground in the appropriate mills and rollers to obtain wettable powders which can be diluted with water to give suspensions of the desired concentration.

Emulsifiable concentrates

The following substances are used to produce (a) a 10%, (b) a 25% and (c) a 50% emulsifiable concentrate:
(a) 10 parts of active substance,
3.4 parts of epoxidised vegetable oil,
3.4 parts of a combination emulsifier consisting of fatty alcohol polyglycol ether and alkylaryl-sulphonate calcium salt,
40 parts of dimethylformamide,
43.2 parts of xylene;
(b) 25 parts of active substance,
2.5 parts of epoxidised vegetable oil,
10 parts of an alkylarylsulphonate/fatty alcohol polyglycol ether mixture,
5 parts of dimethylformamide,
57.5 parts of xylene;
(c) 50 parts of active substance,
4.2 parts of tributylphenol-polyglycol ether,
5.8 parts of calcium-dodecylbenzenesulphonate,
20 parts of cyclohexanone,
20 parts of xylene.

Emulsions of the concentration required can be prepared from these concentrates by dilution with water.

Spray

The following constituents are used to produce (a) a 5% spray and (b) a 95% spray:
(a) 5 parts of active substance,
1 part of epichlorohydrin,
94 parts of ligroin (boiling limites 160°–190° C.);
(b) 95 parts of active substance,
5 parts of eichlorohydrin.

The invention is further illustrated by the following Examples.

EXAMPLE 1

(a) Production of S-triazolo-2-hydroxy-5,7-dimethyl-(1,5-a)-pyrimidine 200 g of 3-amino-5-hydroxy-1,2,3-triazole, 500 ml of concentrated hydrochloric acid and 500 ml of water are refluxed, and at the reflux temperature are added dropwise 250 ml of acetylacetone. After completion of the addition, refluxing is continued for a further three hours. After cooling, the crystals which have formed are filtered off with suction and washed with water. For purification, there is added to the crystal mass in 500 ml of water 25% ammonia, so that the resulting solution remains slightly ammoniacel. The impurities are removed by filtration and precipitation is effected with glacial acetic acid. The crystals are again washed with water and dried at 50° C. in vacuo. There is obtained the compound of the formula

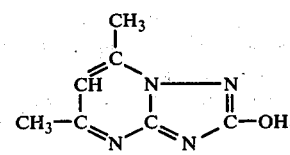

having a melting point of > 350° C.

(b) Production of 0,0-diethyl-0-5,7-dimethyl-s-triazolo-(1,5-a)-pyrimidin-2-yl-thiophosphoric acid ester 10 g of 2-hydroxy-5,7-dimethyl-S-triazolo-(1,5-a)-pyrimidine, 300 ml of methyl ethyl ketone and 8.4 g of finely powdered anhydrous potassium carbonate are refluxed for 2 hours. After the dropwise addition of 11.5 g of diethoxythiophosphoric acid chloride, dissolved in a small amount of methyl ethyl ketone, refluxing is continued for a further 2 hours. In further processing of the reaction mixture, the insoluble salts are filtered off and the solvent is evaporated off. recrystallisation from methanol yields the compound of the formula

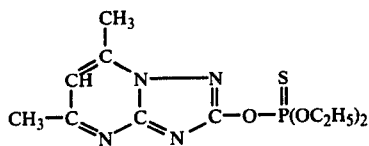

having a melting point of 91–92° C.

NMR analysis: 60 mc/s in CDCl$_3$/TMS: H on the heterocycle: 6.8 ppm; 2-CH$_3$at 2.65 or 2.75 ppm; 2-OCH$_2$- at 4.5 ppm; 2-CH$_3$ at 1.4 ppm.

The following compounds are produced in an analogous manner:

| R | |
|---|---|
| $\overset{O}{\underset{\|}{-}}P(OC_2H_5)_2$ | m.p.: 76–77° C. |
| $\overset{S}{\underset{\|}{-}}P\overset{OC_2H_5}{\underset{C_2H_5}{}}$ | m.p.: 85–86° C. |
| $\overset{S}{\underset{\|}{-}}P\overset{OCH_3}{\underset{NH\,C_3H_7(i)}{}}$ | m.p.: 123–125° C. |
| $\overset{S}{\underset{\|}{-}}P(OCH_3)_2$ | m.p.: 110–112° C. |
| $\overset{S}{\underset{\|}{-}}P(OC_4H_9(n))_2$ | $n_D^{20} = 1,5130$ |
| $\overset{S}{\underset{\|}{-}}P\overset{SC_3H_7(n)}{\underset{OC_2H_5}{}}$ | m.p.: 47–49° C. |
| $\overset{O}{\underset{\|}{-}}P\overset{SC_3H_7(n)}{\underset{OC_2H_5}{}}$ | $n_D^{20} = 1,5348$ |

EXAMPLE 2

(A) Insecticidal stomach-poison action

Cotton plants were sprayed with a 0.05% aqueous emulsion of the active substance (obtained from a 10% emulsifiable concentrate).

After drying of the coating, larvae of *Spodoptera littoralis* in the L$_3$-stage and of *Heliothis virescens* in the L$_3$-stage were placed onto the cottom plants. The test was carried out at 24° C. with 60% relative humidity.

Compounds according to Example 1 exhibited in the above test a good insecticidal stomach-poison action against larvae of *Spodoptera littoralis* and *Heliothis virescens*.

(B) Systemic insecticidal action

In order to determine the systemic action, rooted bean plants (*Vicia faba*) were placed into a 0.01% aqueous solution of the active substance (obtained from a 10% emulsifiable concentrate). After 24 hours, bean aphids (*Aphis fabae*) were placed onto the parts of the plants that had been above the soil. By means of a special device, the bean aphids were protected from the effects of contact and of gas. The test was carried out at 24° C. with 70% relative humidity.

Compounds according to Example 1 exhibited in the above test a systemic insecticidal action against *Aphis fabae*.

EXAMPLE 3

Action against *Chilo suppressalis*

Rice plants of the variety Caloro were planted six plants per pot in plastic pots having an upper diameter of 17 cm, and grown to a height of about 60 cm. Infestation with Chilo suppressalis larvae (L$_1$; 3–4 mm long) was carried out 2 days after application of the active substance in granular form (amount applied = 8 kg of active substance per hectare) to the paddy water. An evaluation of the insecticidal action was made 10 days after application of the granules.

Compounds according to Example 1 exhibited in the above test a good action against *Chilo suppressalis*.

EXAMPLE 4

Acaricidal action

*Phaseolus vulgaris* plants were infested, 12 hours before the test for acaricidal action, with an infested piece of leaf from a mass culture of *Tetranychus urticae*. The transferred mobile stages were sprayed with the emulsified test preparations from a chromatography-sprayer in a manner ensuring no overflow of the spray liquor. An assessment was made after 2 to 7 days, by examination under a binocular microscope, of the living and of the dead larvae, adults and eggs, and the results were expressed as percentages. The treated plants were kept during the "holding time" in greenhouse compartments at 25° C.

Compounds according to Example 1 exhibited in the above test a good action against adults, larvae and eggs of *Tetranychus urticae*.

EXAMPLE 5

Action against soil nematodes

In order to test their action against soil nematodes, the active substances were added to soil infested with root-gall nematodes (*Meloidogyne arenaria*), and intimately mixed with the soil. In one test series, tomato seedlings were planted immediately after preparation of the soil in this manner, and in the other test series tomatoes were sown after a waiting time of 8 days. An assessment of the nematocidal action was made by counting the galls present on the roots 28 days after planting and sowing, respectively.

Active substances according to Example 1 exhibited in this test a good action against *Meloidogyne arenaria*.

EXAMPLE 6

Action against ticks (A) *Rhipicephalus bursa*

For each concentration, 5 adult ticks and 50 tick larvae, respectively, were counted into a small glass test tube, and immersed for 1 to 2 minutes in 2 ml of an aqueous emulsion from a dilution series of 100, 10, 1 and 0.1 ppm of test substance. The tubes were then sealed with a standardised cotton plug and inverted so that the active-substance emulsion could be absorbed by the cotton wool.

The evaluation in the case of the adults was made after 2 weeks and in the case of the larvae after 2 days. There were two repeats for each test.

(B) *Boophilus microplus* (larvae)

With a dilution series analogous to that of Test A, tests were carried out with 20 sensitive larvae and OP-resistant larvae, respectively (resistance is with respect to diazinon compatibility).

Compounds according to Example 1 were effective in these tests against adults and larvae of *Rhipicephalus bursa* and against sensitive and OP-resistant larvae, respectively, of *Boophilus microplus*.

EXAMPLE 7

Action against *Erysiphe graminis* on *Hordeum vulgare*

Barley plants about 8 cm in height were sprayed with a spray liquor produced from wettable powder of the active substance (0.05% of active substance). The treated plants were dusted after 48 hours with conidia of the fungus. The infested barley plants were placed in a greenhouse at about 22° C., and the fungus infestation was assessed after 10 days.

Compounds according to Example 1 were effective in this test against *Erysiphe graminis*.

We claim:

1. A compound of the formula

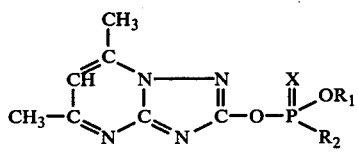

wherein
X represents oxygen or sulphur,
$R_1$ represents $C_1$-$C_6$-alkyl, and
$R_2$ represents $C_1$-$C_6$-alkyl, $C_1$-$C_6$-alkoxy, $C_1$-$C_6$-alkylthio, $C_1$-$C_6$-alkylamino or di-$C_1$-$C_6$-alkylamino.

2. A compound according to claim 1, wherein $R_1$ represents methyl, ethyl or n-butyl, and $R_2$ represents ethyl, methoxy, ethoxy, n-propylthio, isopropylamino or n-butoxy.

3. The compound according to claim 2 of the formula

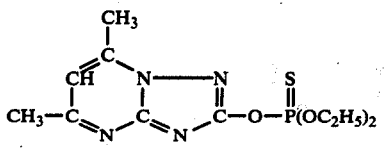

4. The compound according to claim 2 of the formula

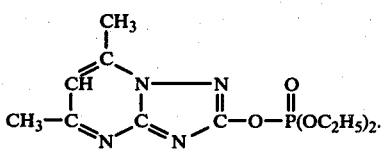

5. The compound according to claim 2 of the formula

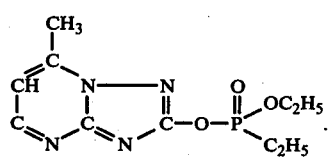

6. The compound according to claim 2 of the formula

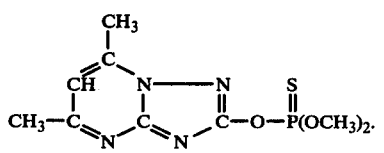

7. The compound according to claim 2 of the formula

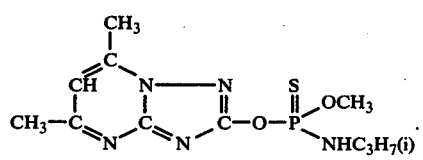

8. The compound according to claim 2 of the formula

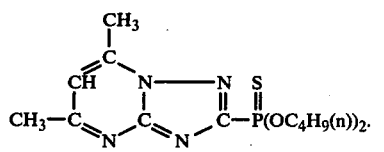

9. The compound according to claim 2 of the formula

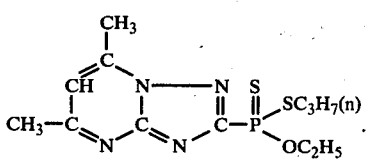

10. The compound according to claim 2 of the formula
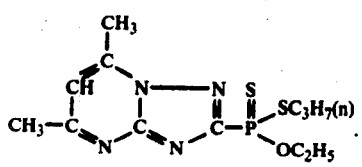
11. An insecticidal and acaricidal composition which comprises a compound according to claim 1 as active ingredient, and a carrier.
12. A method for combating insects and and acarides which comprises applying thereto an insecticidally or acaricidally effective amount of a compound according to claim 1.
* * * * *